United States Patent [19]

Muller et al.

[11] 4,220,772

[45] Sep. 2, 1980

[54] PROCESS FOR THE PREPARATION OF OXADIAZOLOPYRIMIDINE DERIVATIVES

[75] Inventors: Jean-Claude Muller, Rixheim, France; Henri Ramuz, Birsfelden, Switzerland

[73] Assignee: Hoffmann-La Roche Inc., Nutley, N.J.

[21] Appl. No.: 55,230

[22] Filed: Jul. 6, 1979

[30] Foreign Application Priority Data

Jul. 21, 1978 [CH] Switzerland ............... 7910/78

[51] Int. Cl.$^2$ ............... A61K 31/505; C07D 498/04
[52] U.S. Cl. ............... 544/255; 424/251; 544/323; 544/324; 546/330
[58] Field of Search ............... 544/255

[56] References Cited

U.S. PATENT DOCUMENTS

| 4,150,131 | 4/1979 | Muller et al. | 424/251 |
| 4,150,132 | 4/1979 | Muller et al. | 424/251 |

*Primary Examiner*—Alton D. Rollins
*Assistant Examiner*—Lisa Jones
*Attorney, Agent, or Firm*—Jon S. Saxe; George M. Gould; William G. Isgro

[57] ABSTRACT

A process for preparing oxadiazolopyrimidines of the formula

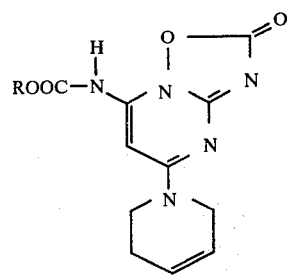

I wherein R is alkyl or alkoxyalkyl, by reacting a compound of the formula

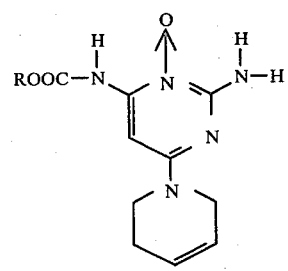

II wherein R is as set forth above, with phosgene, is described.

4 Claims, No Drawings

PROCESS FOR THE PREPARATION OF OXADIAZOLOPYRIMIDINE DERIVATIVES

BRIEF SUMMARY OF THE INVENTION

The invention relates to a process for preparing compounds of the formula

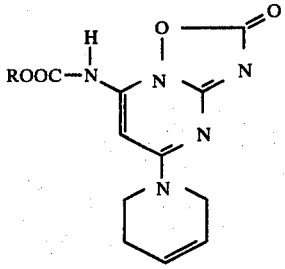

wherein R is alkyl or alkoxyalkyl,
and salts thereof, which comprises reacting a compound of the formula

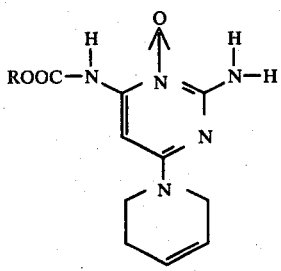

wherein R is alkyl or alkoxylalkyl,
with phosgene and, if desired, converting a resulting compound of formula I into a salt.

In another aspect, the invention relates to compounds of formula II.

In yet another aspect, the invention relates to compounds of the formula

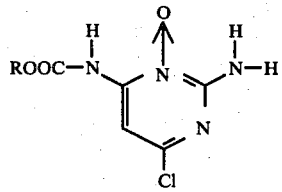

wherein R is alkyl or alkoxyalkyl.

DETAILED DESCRIPTION OF THE INVENTION

The oxadiazolopyrimidine derivatives obtained in accordance with the process of the invention are compounds of the formula

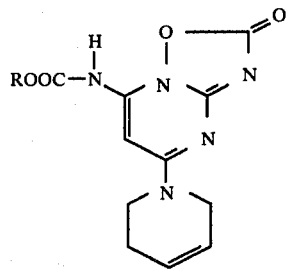

wherein R is alkyl or alkoxyalkyl,
and salts thereof.

As used herein, the term "alkyl", alone or in combination, denotes a straightchain and branched-chain saturated hydrocarbon containing 1–8 carbon atoms, for example, methyl, ethyl, n-propyl, isopropyl, n-butyl, isobutyl, tert.butyl and the like. The term "alkoxy" denotes an alkyl ether group in which the "alkyl" moiety is as described above. Exemplary are methoxy, ethoxy, n-propoxy, tert.butoxy and the like.

Preferred compounds of formula I are those in which R is alkyl, preferably alkyl of 1–4 carbon atoms. The compound of formula I in which R is methyl, i.e., methyl 5-[3,6-dihydro-1(2H)-pyridyl]-2-oxo-2H-[1,2,4]oxadiazolo[2,3-a]-pyrimidine-7-carbamate, is particularly preferred.

In accordance with the invention, the oxadiazolopyrimidine derivatives, that is, the compounds of formula I and their salts, are prepared by reacting a compound of the formula

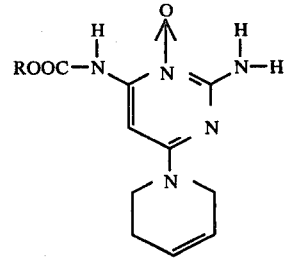

wherein R is as previously described,
with phosgene and, if desired, converting a resulting compound of formula I into a salt or converting a salt into a different salt.

The reaction of a compound of formula II with phosgene is carried out in a known manner in the presence of a solvent or solvent mixture. Examples of solvents which can be used are aromatic hydrocarbons, for example, benzene, toluene and xylene; chlorinated hydrocarbons, for example, methylene chloride and chloroform; and the like or mixtures thereof. The reaction is conveniently carried out at atmospheric pressure and at a temperature in the range of from about −20° C. to 50° C., preferably at about 0° C., in the presence of an acid-binding agent. Suitable acid-binding agents are tertiary organic bases, for example, triethylamine, ethyldiisopropylamine, pyridine and the like.

The starting materials of formula II also form part of the invention. They are not only important intermediates in the preparation of the oxadiazolopyrimidine derivatives provided by this invention, but also themselves possess vasodilating and/or blood pressure-lowering properties. They can be prepared, for example, by reacting 2,4-diamino-6-[3,6-dihydro-1(2H)-pyridyl]-pyrimidine-3-oxide or the tautomeric 6-amino-4-[3,6-dihydro-1(2H)-pyridyl]-1,2-dihydro-1-hydroxy-2-iminopyrimidine and 2-amino-4-[3,6-dihydro-1(2H)-1,6-dihydro-1-hydroxy-6-imino-pyrimidine of the formulas

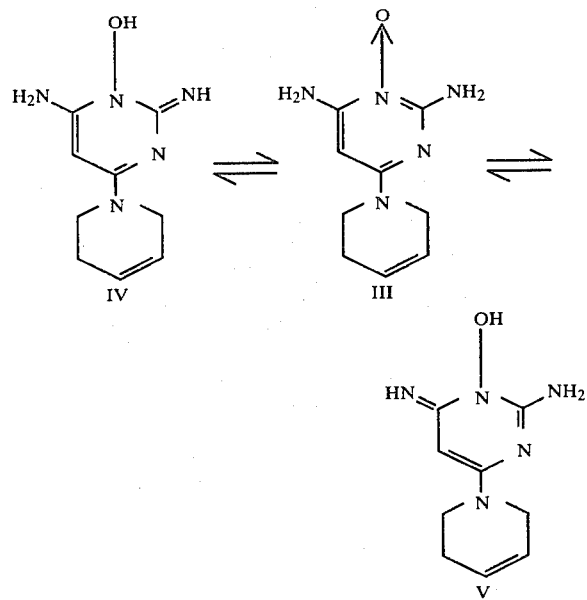

with a chloroformic acid ester of the formula

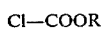  VI wherein R is as previously described.

The above reaction is carried out in an inert solvent or solvent mixture in the presence of an acid-binding agent. Suitable solvents for the present purpose are chlorinated hydrocarbons, for example, methylene chloride and chloroform; ethers, for example, diethyl ether, tetrahydrofuran and dioxane; dimethylformamide and the like; or mixtures thereof. The reaction can also be carried out in a water-containing solvent or in the presence of water in a two-phase system, for example, methylene chloride/water. Examples of acid-binding agents which can be used are bases, for example, triethylamine, ethyldiisopropylamine, dimethylamine, pyridine, alkali hydroxides and the like. When the reaction is carried out in the presence of a liquid base, it can also serve as the solvent. The reaction is conveniently carried out at a temperature in the range of from about −10° C. to about room temperature, preferably in the range of from about 0° C. to 10° C.

When the reaction is carried out using 1 mol equivalent of a chloroformic acid ester of formula VI, then the desired compound of formula II is obtained directly. On the other hand, when the reaction is carried out using an excess of a chloroformic acid ester of formula VI, there is obtained the dicarbamate of the formula

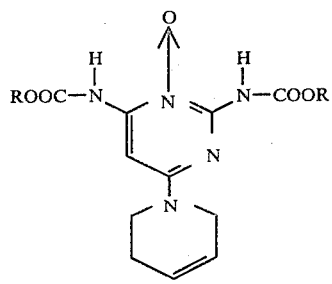  VII wherein R is as previously described, corresponding to the compound of formula II. The dicarbamate can be converted into the desired compound of formula II by treatment with an aqueous inorganic base such as an alkali metal hydroxide, for example, sodium hydroxide or potassium hydroxide; an alkaline earth metal hydroxide, for example, barium hydroxide or calcium hydroxide; a carbonate, for example, potassium carbonate or sodium carbonate; or a bicarbonate, for example, sodium bicarbonate; and the like. The treatment with a base is carried out in the presence of a solvent or solvent mixture at a temperature in the range of from about −20° C. to 50° C., preferably in the range of from about 0° C. to room temperature. Examples of solvents which can be used are aromatic hydrocarbons, for example, benzene, toluene and xylene; chlorinated hydrocarbons, for example, methylene chloride and chloroform; alcohols, for example, methanol and ethanol; acetone; dimethylformamide; dimethylsulfoxide; and the like or mixtures thereof.

Alternatively, the starting materials of formula II can be prepared by reacting a 2-amino-4-alkylcarbamate-6-chloropyrimidine-3-oxide of the formula

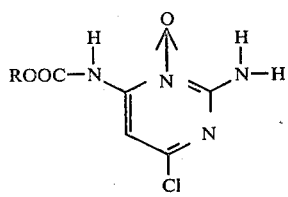  VIII wherein R is as previously described, with 1,2,5,6-tetrahydropyridine.

The reaction is carried out in an inert solvent or solvent mixture. Suitable solvents for this purpose are chlorinated hydrocarbons, for example, methylene chloride and chloroform; aromatic hydrocarbons, for example, toluene and xylene; and the like or mixtures thereof. The reaction is preferably carried out under an atmosphere of inert gas, preferably argon or nitrogen, at a temperature in the range of from about 0° C. to 50° C., preferably at room temperature. Excess 1,2,5,6-tetrahydropyridine can be used in place of an inert solvent.

The compounds of formula II can also be prepared from the compounds of formula I by treatment with an aqueous inorganic base such as an alkali metal hydroxide, for example, sodium hydroxide or potassium hydroxide; an alkaline earth metal hydroxide, for example, barium hydroxide or calcium hydroxide; a carbonate, for example, potassium carbonate or sodium carbonate; or a bicarbonate, for example, sodium bicarbonate; and the like at a temperature in the range of from about 0° C. to room temperature, preferably at room temperature.

The compound of formula III or its tautomers of formulas IV and V can be prepared in an analogous manner to the preparation of known compounds. Two processes are illustrated in the following Formula Scheme. Regarding the precise reaction conditions, reference is made to the detailed Examples hereinafter.

Formula Scheme

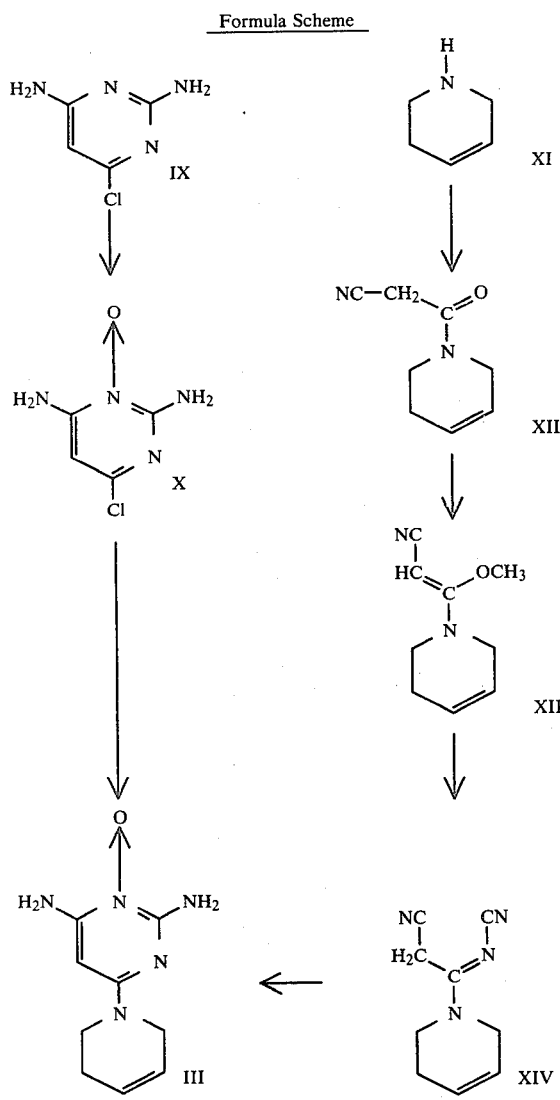

The compounds of formula VIII hereinbefore also form part of the invention. They can be prepared by reacting 2,4-diamino-6-chloropyrimidine-3-oxide of formula X with 1 mol equivalent of a chloroformic acid ester of formula VI. The reaction is carried out under the conditions described earlier in connection with the reaction of a compound of formula III or a tautomer thereof of formula IV or V with a chloroformic acid ester of formula VI.

The compounds of formula I can be converted into salts; for example, by treatment with an inorganic base, such as, an alkali metal hydroxide, for example, sodium hydroxide or potassium hydroxide; an alkaline earth metal hydroxide, for example, calcium hydroxide; or with an inorganic base such as a monoalkylamine, for example, methylamine, a dialkylamine, for example, dimethylamine; a trialkylamine, for example, triethylamine; a basic amino acid, for example, arginine; piperidine; an azabicyclo-octane or -nonane {e.g., 3-azabicyclo[3.2.1]octane or 3-azabicyclo[3.2.2]nonane} and the like. Salts of the compounds of formula I can also be prepared by double-decomposition of a suitable salt. Among the salts of the compounds of formula I, the pharmaceutically acceptable salts are preferred.

The oxadiazolopyrimidine derivatives provided by the present invention possess long-lasting and valuable vasodilating and/or blood pressure-lowering properties and can accordingly be used for the treatment of vascular-conditioned hypertension or also as vasodilators in peripheral blood supply disorders.

The blood pressure-lowering activity can be determined in conscious, spontaneous hypertensive rats by the following method:

The systolic blood pressure and the heart frequency are measured twice before administration of the test substance. The test substance is administered by means of an oesophageal probe twice daily, morning and afternoon. Both parameters are measured 1, 3, 6 and 24 hours after the administration, and the percentage variations to the control values are calculated. The systolic blood pressure is measured indirectly in the tail artery of the rat by the method of Gerold et al. (Helv. Physiol. Acta 24: 58–69, 1966; Arzneimittelforschung 18: 1285–1287, 1968).

The vasodilating activity can be determined in conscious, chronic implanted dogs by the following method:

Female cross-bred sheepdogs of about 25 kg. body-weight are implanted under sterile precautions with an electromagnetic flow probe and a vessel constrictor around the abdominal aorta. The zero-flow is determined by pinching-off the vessel by means of an occluder. The heart frequency, triggered from the pulsating flow, and the aorta flow are continuously recorded during the first three hours after administration of the test substance and after 6, 24, 48 and 72 hours, the dogs in each case lying still, but not being sedated, in an experimental box for the measurement. The test substances are administered orally in gelatin capsules.

The results obtained are compiled in the following Tables, in each case the maximum percentage deviation from the control values as well as the duration of activity in hours [calculated as the average value from 5 (rat) or 3 (dog) experiments] are provided.

Table I

| Compound | Dosage mg/kg p.o. | Blood pressure | | Heart frequency | |
|---|---|---|---|---|---|
| | | Δ% | Duration of activity in hours | Δ% | Duration of activity in hours |
| | 3 | + 9 | >24 | − 5 | >24 |
| A | 10 | −20 | >24 | +12 | >24 |
| | 30 | −19 | >24 | − 7 | > 3 |
| | 100 | −29 | >24 | +16 | >24 |

Table II

| Compound | Dosage mg/kg p.o. | AABF* | | Heart frequency | |
|---|---|---|---|---|---|
| | | Δ% | Duration of activity in hours | Δ% | Duration of activity in hours |
| | 1 | + 21 | >24 | + 3 | 6 |
| | 3 | + 51 | >24 | + 8 | 24 |
| A | 10 | + 88 | >24 | +19 | >24 |

Table II-continued

| Compound | Dosage mg/kg p.o. | AABF* Δ% | AABF* Duration of activity in hours | Heart frequency Δ% | Heart frequency Duration of activity in hours |
|---|---|---|---|---|---|
| | 30 | +111 | >48 | +29 | >72 |

*AABF = abdominal aortic blood flow
A = Methyl 5-[3,6-dihhydro-1(2H)-pyridyl]-2-oxo-2H-[1,2,4]-oxadiazolo[2,3-a]pyrimidine-7-carbamate The compounds of formula I and their pharmaceutically acceptable salts can be used as medicaments; for example, in the form of pharmaceutical preparations which contain them in association with a compatible pharmaceutical carrier material. This carrier material can be an organic or inorganic inert carrier material suitable for enteral or parenteral administration, for example, water, gelatin, gum arabic, lactose, starch, magnesium stearate, talc, vegetable oils, polyalkyleneglycols, and the like. The pharmaceutical preparations can be made up in solid form, for example, tablets, dragees, suppositories or capsules, or in liquid form, for example, solutions, suspensions or emulsions. The pharmaceutical preparations may be sterilized and/or may contain adjuvants, such as preserving, stabilizing, wetting or emulsifying agents, salts for varying the osmotic pressure or buffers. They can also contain still other therapeutically valuable substances.

The daily dosage for oral administration lies in the range of from about 10 mg. to 500 mg. and in the case of intravenous administration lies in the range of from about 1 mg. to 50 mg. It will be appreciated that the aforementioned dosages are given by way of examples and can be altered according to the severity of the condition to be treated and according to the judgment of the treating practitioner.

The Examples which follow further illustrate the invention. All temperatures are in degrees Centigrade, unless otherwise mentioned.

EXAMPLE 1

Preparation of pure methyl 5-[3,6-dihydro-1(2H)-pyridyl]-2-oxo-2H-[1,2,4]-oxadiazolo[2,3-a]pyrimidine-7-carbamate 53 Mg. of methyl 2-amino-6-[3,6-dihydro-1(2H)-pyridyl[-4-pyrimidinecarbamate-3-oxide are dissolved in 5 ml. of methylene chloride. The solution is cooled to 0° C. and treated with 0.2 ml. of triethylamine and 0.12 ml. of 20% phosgene in toluene. The mixture is stirred for 30 minutes and then treated with 0.5 ml. of concentrated sodium hydroxide and 10 ml. of water. After stirring for 15 minutes, the two phases are separated, and the organic phase is again washed with water. The combined aqueous phases are acidified with hydrochloric acid, there being obtained pure methyl 5-[3,6-dihydro-1(2H)-pyridyl]-2oxo-2H-[1,2,4]-oxadiazolo[2,3-a]pyrimidine-7-carbamate having a melting point of 213°–214° C.

The methyl 2-amino-6-[3,6-dihydro-1(2H)-pyridyl]-4-pyrimidinecarbamate-3-oxide used as the starting material can be prepared as follows:

(A) 144.5 g. of 2,4-diamino-6-chloropyrimidine are suspended in 2000 ml. of ethanol. While stirring, the suspension is warmed to 35° C. (about 15 minutes), the greater part of the substance passing into solution. The mixture is then cooled to 6°–8° C. and, at this temperature, there are added dropwise within the course of 40 minutes 175 ml. of 40% peracetic acid in glacial acetic acid. After completion of the addition, the mixture is stirred at 6°–8° C. for a further 30 minutes. The mixture is then left to warm up to room temperature and stirred at this temperature for 3 hours. 2000 Ml. of petroleum ether are then added, the mixture is left to stir for 1 hour and then left to stand overnight. The separated precipitate is filtered off, back-washed with 200 ml. of petroleum ether and dried under reduced pressure, there being obtained 2,4-diamino-6-chloropyrimidine-3-oxide. Recrystallization yields analytically-pure product having a melting point of 193° C.

The aforementioned 2,4-diamino-6-chloropyrimidine-3-oxide can also be prepared as follows:

75 g. of 2,4-diamino-6-chloropyrimidine are dissolved in 1500 ml. of ethanol at 35° C. The solution is cooled to −10° C. and a solution of 100 g. of 3-chloro-perbenzoic acid in 500 ml. of ethanol is slowly added dropwise in the course of 1 hour. The suspension is subsequently stirred at −10° C. for 7 hours and left to stand at 5° C. overnight. The suspension is neutralized with 24 g. of sodium hydroxide in 100 ml. of water. The solid material is filtered off and recrystallized from ethanol, there being obtained pure 2,4-diamino-6-chloropyrimidine-3-oxide.

155 g. of 2,4-diamino-6-chloropyrimidine-3-oxide are mixed and stirred under an argon atmosphere with 640 ml. of o-xylene and 260 ml. of 1,2,5,6-tetrahydropyridine. The mixture is then heated to reflux for 30 minutes, the internal temperature rising from 115° C. to 123° C. The mixture is then cooled to 5° C., treated with 40 g. of sodium hydroxide in 400 ml. of water and stirred at 5° C. for 1 hour. The precipitate formed is filtered off, washed with 200 ml. of water and recrystallized from 3000 ml. of water, there being obtained pure 2,4-diamino-6-[3,6-dihydro-1(2H)-pyridyl]pyrimidine-3-oxide having a melting point of 263°–265° C. (decomposition).

45 G. of 2,4-diamino-6-[3,6-dihydro-1(2H)-pyridyl]-pyrimidine-3-oxide are mixed in 600 ml. of methylene chloride with 90 ml. of triethylamine and cooled to 5° C. 90 Ml. of chloroformic acid methyl ester are added dropwise while stirring. The mixture is stirred at 5° C. for 30 minutes and at room temperature for 18 hours. Then, the mixture is treated with 100 ml. of methanol and subsequently extracted with 400 ml. of methylene chloride, washed with water, dried over sodium sulfate and evaporated under reduced pressure. Recrystallization of the residue from methanol yields dimethyl 6-[3,6-dihydro-1(2H)-pyridyl]-2,4-pyrimidinedicarbamate-3-oxide having a melting point of 202°–203° C.

The last-mentioned compound can also be prepared as follows:

20 G. of 2,4-diamino-6-[3,6-dihydro-1(2H)-pyridyl]-pyrimidine-3-oxide are suspended and stirred in 100 ml. of methylene chloride and 200 ml. of water. While cooling, there are simultaneously added dropwise 25 ml. of chloroformic acid methyl ester in 50 ml. of methylene chloride and 30 ml. of 28% sodium hydroxide so that the pH value is held between 7.5 and 8.5. After completion of the addition, the suspension is stirred for a further hour, and the precipitate formed is subsequently filtered off. The filtrate is washed with methylene chloride and thereafter combined with the precipitate. The whole is recrystallized from methylene chloride/methanol, there being obtained dimethyl 6-[3,6-dihydro-1(2H)-pyridyl]-2,4-pyrimidinedicarbamate-3-oxide having a melting point of 202°–206° C. (decomposition).

The aforementioned dimethyl 6-[3,6-dihydro-1(2H)-2,4-pyrimidinedicarbamate-3-oxide can also be prepared as follows:

56 g. of 2,4-diamino-6-chloropyrimidine-3-oxide in 500 ml. of dimethylformamide and 100 ml. of triethylamine are cooled to 0° C. 80 Ml. of chloroformic acid methyl ester are added dropwise while stirring within 1 hour. After completion of the addition, the mixture is stirred for 48 hours. The precipitate is filtered off, suspended in a mixture of 2500 ml. of methylene chloride and 500 ml. of methanol and stirred for 80 minutes. The insoluble residue is filtered off and dried, there being obtained pure dimethyl 6-chloro-2,4-pyrimidinedicarbamate-3-oxide having a melting point of 204° C. (decomposition). The organic phase is washed with water and concentrated, a further amount of pure material being obtained.

A suspension of 10 g. of dimethyl 6-chloro-2,4-pyrimidinedicarbamate-3-oxide in 40 ml. of methylene chloride is treated with 20 ml. of 1,2,5,6-tetrahydropyridine and stirred at room temperature under an argon atmosphere for 16 hours. The precipitate formed is filtered off and recrystallized from a mixture of methylene chloride and methanol, there being obtained pure dimethyl 6-[3,6-dihydro-1(2H)-pyridyl]-2,4-pyrimidinedicarbamate-3-oxide having a melting point of 203° C.

10 G. of dimethyl 6-[3,6-dihydro-1(2H)-pyridyl]-2,4-pyrimidinedicarbamate-3-oxide are dissolved in 350 ml. of chloroform and 100 ml. of methanol. The solution obtained is treated with 5 g. of sodium carbonate in 100 ml. of water and the resulting mixture is stirred at room temperature for 80 hours. The mixture is then diluted with 250 ml. of water and adjusted to pH 12.5 with concentrated sodium hydroxide. The mixture is then stirred for 30 minutes and then the two phases are separated. The aqueous phase is extracted twice with methylene chloride. The combined organic extracts are dried over magnesium sulfate and evaporated to dryness under reduced pressure. The residue is chromatographed over silica gel using a mixture of chloroform and ethanol (90:10) for the elution, there being obtained pure methyl 2-amino-6-[3,6-dihydro-1(2H)-pyridyl]-4-pyrimidinecarbamate-3-oxide having a melting point of 174°–176° C.

(B) 20 G. of 2,4-diamino-6-[3,6-dihydro-1(2H)-pyridyl]-pyrimidine-3-oxide are suspended and stirred in 140 ml. of methylene chloride and 120 ml. of water. While cooling, there are simultaneously added dropwise 8 ml. of chloroformic acid methyl ester in 20 ml. of methylene chloride and sufficient 28% sodium hydroxide so that the pH value is held between 7.0 and 7.5. After completion of the addition, the mixture is stirred for a further 1 hour and the residue is subsequently filtered off. The two phases obtained are separated and the organic phase is treated for 1 hour while stirring at 0° C. with 150 ml. of 1-N sodium hydroxide. The mixture obtained is treated with 20 ml. of methanol and the two phases are separated. The aqueous phase is extracted twice with 200 ml. of methylene chloride and the combined organic extracts are dried over sodium sulfate. By evaporation of the solvent there is obtained pure methyl 2-amino-6-[3,6-dihydro-1(2H)-pyridyl]-4-pyrimidinecarbamate-3-oxide having a melting point of 174°–176° C.

(C) 10 G. of 2,4-diamino-6-chloropyrimidine-3-oxide are suspended while stirring in 100 ml. of dimethylformamide and 10 ml. of triethylamine. The suspension is cooled to about 0° C. and 5 ml. of chloroformic acid methyl ester are added dropwise in the course of 10 minutes. The mixture is then stirred at about 0° C. for 45 minutes and subsequently at room temperature for 18 hours. The precipitated product is filtered off, and the filtrate is concentrated in a high vacuum. The residue is dissolved in methylene chloride and methanol and the insoluble material is filtered off. The filtrate is again concentrated and the residue is chromatographed over silica gel, there being obtained pure 2-amino-4-methylcarbamate-6-chloropyrimidine-3-oxide having a melting point of 220°–221° C.

1.09 G. of 2-amino-4-methylcarbamate-6-chloropyrimidine-3-oxide are treated while stirring with 10 ml. of chloroform. 1.5 Ml. of 1,2,5,6-tetrahydropyridine in 2 ml. of chloroform are slowly added dropwise to this suspension, the temperature rising to 40° C. The mixture is then stirred at 50° C. for 3 hours and then cooled. The cooled solution is diluted with chloroform and washed with water. The organic solution is separated, dried over magnesium sulfate and concentrated under reduced pressure. The residue obtained is recrystallized from methylene chloride and diethyl ester, there being obtained methyl 2-amino-6-[3,6-dihydro-1(2H)-pyridyl]-4-pyrimidinecarbamate-3-oxide having a melting point of 174°–176° C.

EXAMPLE 2

Preparation of the 3-azabicyclo[3.2.2.]nonane salt of methyl 5-[3,6-dihydro-1(2H)-pyridyl]-2-oxo-2H-[1,2,4]oxadiazolo[2,3-a]pyrimidine-7-carbamate 2 G. of methyl 5-[3,6-dihydro-1(2H)-pyridyl]-2-oxo-2H-[1,2,4]oxadiazolo[2,3-a]pyrimidine-7-carbamate are suspended in acetonitrile and treated with 1.6 g. of 3-azabicyclo[3.2.2]nonane in 20 ml. of acetonitrile. There is first obtained a clear solution, but there very rapidly precipitates out the corresponding 3-azabicyclo[3.2.2-]nonane salt, the structure of which is confirmed by X-ray structural analysis. The pure salt having a melting point of 164°–168° C. is obtained by recrystallization.

EXAMPLE 3

Preparation of the sodium salt of methyl 5-[3,6-dihydro-1(2H)-pyridyl]-2-oxo-2H-[1,2,4]-oxadiazolo[2,3-a]pyrimidine-7-carbamate 3 G. of methyl 5-[3,6-dihydro-1(2H)-pyridyl]-2-oxo-2H-[1,2,4]oxadiazolo[2,3-a]-pyrimidine-7-carbamate are dissolved in 2-N sodium hydroxide and the solution is left to stand. Upon cooling there precipitates out the corresponding sodium salt which is recrystallized from acetonitrile and water and which begins to decompose from 145° C.

EXAMPLE 4

Preparation of pure 2-methoxyethyl 5-[3,6-dihydro-1(2H)-pyridyl]-2-oxo-2H-[1,2,4]oxadiazolo[2,3-a]pyrimidine-7-carbamate 2 G. of 2-methoxyethyl 2-amino-6-[3,6-dihydro-1(2H)-pyridyl]-4-pyrimidinecarbamate-3-oxide are dissolved at 0° C. in 15 ml. of chloroform and 3.7 ml. of triethylamine. The cold stirred mixture is treated with 3.2 ml. of 20% phosgene in toluene. The mixture is then stirred for 4 hours, acidified with hydrochloric acid, washed with water and extracted with methylene chloride. The organic phase is dried over magnesium sulfate and the solvent is distilled off under reduced pressure. The residue obtained is crystallized from methylene chloride and ether, there being obtained pure 2-methoxyethyl 5-[3,6-dihydro-1(2H)-pyridyl]-2-oxo-2H-[1,2,4]oxadiazolo[2,3-a]-pyrimidine-7-carbamate having a melting point of 195°–196° C.

The 2-methoxyethyl 2-amino-6-[3,6-dihydro-1(2H)-pyridyl]-4-pyrimidinecarbamate-3-oxide used as the starting material can be prepared as follows:

5 G. of 2,4-diamino-6-chloropyrimidine-3-oxide are suspended in 50 ml. of dimethylformamide and 5 ml. of triethylamine and cooled to 0° C. while stirring. 4.3 G. of chloroformic acid 2-methoxyethyl ester are added dropwise to the cold suspension in the course of 15 minutes. The mixture is cooled for 2 hours and then stirred at room temperature for 16 hours. The solvent is distilled off at 25° C. in a high vacuum and the residue is digested with methylene chloride. The precipitate obtained is filtered off and washed with methylene chloride, methanol and water. The filtrate is washed with water and dried over sodium sulfate. By concentrating the solvent, there is obtained pure 2-methoxyethyl 2-amino-6-chloro-4-pyrimidinecarbamate-3-oxide having a melting point of 176°–178° C. Additional material is obtained by subjecting the mother liquor to chromatographical separation on silica gel.

2.5 G. of 2-methoxyethyl 2-amino-6-chloro-4-pyrimidinecarbamate-3-oxide are mixed under argon with 3 ml. of 1,2,5,6-tetrahydropyridine and 25 ml. of chloroform. The mixture is stirred at 45° C. for 12 hours, then cooled and washed with 15 ml. of water. The product is extracted with chloroform, the organic phase is dried over sodium sulfate and the solvent is distilled off under reduced pressure. The residue obtained is crystallized from methylene chloride/ether, there being obtained pure 2-methoxyethyl 2-amino-6-[3,6-dihydro-1(2H)-pyridyl]-4-pyrimidinecarbamate having a melting point of 136° C.

We claim:

1. A process for the preparation of a compound of the formula

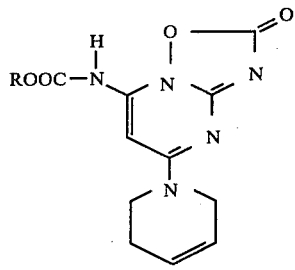

wherein R is alkyl of one to eight carbon atoms or alkoxyalkyl wherein the alkoxy or alkyl moiety has one to eight carbon atoms,
or salt thereof, which comprises reacting a compound of the formula

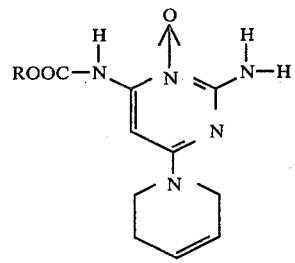

wherein R is as set forth above,
with phosgene and, if desired, converting a resulting compound of formula I into a salt.

2. A process in accordance with claim 1, wherein R is alkyl of one to eight carbon atoms.

3. A process in accordance with claim 2, wherein alkyl contains 1–4 carbon atoms.

4. A process in accordance with claim 3, wherein methyl 5-[3,6-dihydro-1(2H)-pyridyl]-2-oxo-2H-[1,2,4]oxadiazolo[2,3-a]pyrimidine-7-carbamate is prepared.

* * * * *